United States Patent
Sharpe

(10) Patent No.: US 8,014,063 B2
(45) Date of Patent: Sep. 6, 2011

(54) OPTICAL PROJECTION TOMOGRAPHY

(75) Inventor: James Alexander Sharpe, Edinburgh (GB)

(73) Assignee: Medical Research Council (GB)

(*) Notice: Subject to any disclaimer, the term of this patent is extended or adjusted under 35 U.S.C. 154(b) by 1493 days.

(21) Appl. No.: 10/522,924

(22) PCT Filed: Aug. 29, 2003

(86) PCT No.: PCT/GB03/03746
§ 371 (c)(1),
(2), (4) Date: Sep. 26, 2005

(87) PCT Pub. No.: WO2004/020997
PCT Pub. Date: Mar. 11, 2004

(65) Prior Publication Data
US 2006/0093200 A1    May 4, 2006

(30) Foreign Application Priority Data

Aug. 30, 2002 (GB) .................. 0220156.4
Nov. 27, 2002 (GB) .................. 0227649.1

(51) Int. Cl.
*G02B 21/00* (2006.01)

(52) U.S. Cl. .......... 359/368; 359/363
(58) Field of Classification Search .......... 359/368–390, 359/363
See application file for complete search history.

(56) References Cited

U.S. PATENT DOCUMENTS 5,148,022 A * 9/1992 Kawaguchi et al. ..... 250/339.06
6,043,932 A * 3/2000 Kusunose ............... 359/368
7,227,630 B1 * 6/2007 Zavislan et al. ......... 356/244

FOREIGN PATENT DOCUMENTS

JP    04-122248 A       4/1992
WO    WO-02/095476 A2   11/2002

* cited by examiner

*Primary Examiner* — Thong Nguyen
(74) *Attorney, Agent, or Firm* — Barnes & Thornburg LLP

(57) ABSTRACT

Apparatus for obtaining an image of a specimen (6) by optical projection tomography comprises a confocal microscope which produces a light beam which scans the specimen (6) whilst the latter is supported in a rotary stage (7). Light passing through the specimen is passed through a convex lens (8) which directs, onto a central light detector of an array of detectors (9), light which exits or by-passes the specimen parallel to the beam incident on the specimen.

6 Claims, 4 Drawing Sheets

OPTICAL PROJECTION TOMOGRAPHY

FIELD OF THE INVENTION

This invention relates to optical projection tomography.

BACKGROUND TO THE INVENTION

Optical projection tomography is a technique for producing three-dimensional images of specimens, one example being disclosed in the applicant's specification WO 02/095476. The invention aims to provide a different way of optically processing the light emanating from the specimen, with a view to increasing the content and quality of information obtained from the specimen.

SUMMARY OF THE INVENTION

According to one aspect of the invention apparatus for obtaining an image of a specimen by optical projection tomography comprises light scanning means, a rotary stage for rotating the specimen to be imaged, an optical system and a light detector, wherein light from the scanning means scans the specimen and the optical system is operative, throughout the scanning movement of the light, to direct onto the detector only light which exits or by-passes the specimen parallel to the beam incident on the specimen.

The optical system is preferably a convex lens which causes convergence of light incident thereon but directs onto the detector light exiting the specimen parallel to the beam incident on the specimen. A concave mirror or diffraction grating could be used instead of the convex lens.

In a preferred embodiment, the light scanning means form part of a confocal scanning microscope and the rotary stage includes a stationary chamber within which the specimen is suspended.

The light detector may be a localised detector positioned, so as to receive only light which exits or by-passes the specimen at the same angle as the beam incident on the specimen.

However, the light detector may form part of a one-dimensional, i.e. linear, array. In this case, one detector of the array constitutes the light detector and the other detectors of the assay constitute auxiliary detectors which detect scattered and/or refracted light. The intensities of light received by the auxiliary detectors can be used to provide information on the spatial distribution of refractive/scattering characteristics within the specimen.

This approach can be extended to provide a two-dimensional array of detectors, with one detector constituting the light detector and the other detectors constituting auxiliary detectors which detect scattered and/or refracted light in the additional planes.

According to another aspect of the invention there is provided an optical system for use in apparatus for obtaining an image in optical projection tomography, the optical system receiving light from a specimen scanned by a light beam and being operative to direct onto a detector only light which exits or by-passes the specimen parallel to the beam incident on the specimen.

According to a yet further aspect of the invention there is provided a method of obtaining an image of a specimen in optical projection tomography, the method comprising moving a light beam across the specimen with a scanning motion, passing the light emanating from the specimen onto a detector which, throughout the scanning movement of the light, detects light which exits or by-passes the specimen parallel to the beam incident on the specimen.

In the simplest method, there is no optical power between the specimen and the detector, spatial discrimination being achieved through the positioning of the detector.

According to another aspect of the present invention, there is provided a method of performing any one or more of the analyses or procedures listed hereunder comprising use of a method or apparatus of any of the aspects set out above.

BRIEF DESCRIPTION OF THE DRAWINGS

The invention will now be described, by way of example, with reference to the accompanying drawings, in which.

DETAILED DESCRIPTION OF THE DRAWINGS

Figure 1:
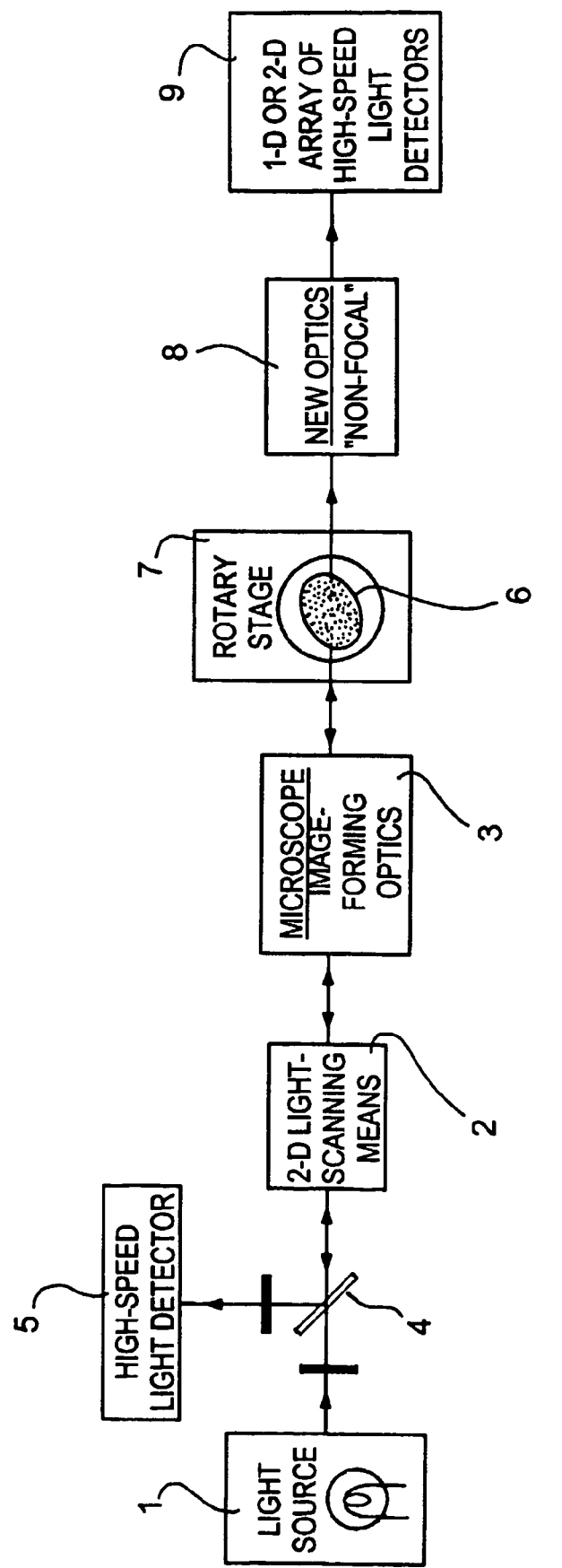
FIG. 1 is a diagram of the apparatus forming the preferred embodiment of the invention.

Referring to FIG. 1, the apparatus comprises a light source 1 (in the form of a laser) which supplies light to a two-dimensional light scanning means 2, the scanning mechanism of which has a dual mirror system. Light with a scanning motion is fed through image-forming optics 3. A dichroic mirror 4 interposed between the light source 1 and the scanning means 2 directs returned light to a high speed light detector 5. The components 1 to 5 may be provided by a confocal light-scanning microscope.

Light from the optics 3 passes through a specimen 6 which is rotated within, and supported by, a rotary stage 7. The rotary stage 7 rotates the specimen to successive indexed positions at each of which one complete scan of the excitation light is undertaken whilst the specimen is stationary. After passing through the specimen 6, the light is processed by an optical system 8 which directs the light to a one-dimensional or two-dimensional array of high speed light detectors 9.

In fluorescence mode, light from the specimen 6 is returned through the optics 3 and the scanning means 2 and thence, via the mirror 4, to the high speed light detector 5. It is in the transmission mode, to be described, that the new arrangement of optics and detectors is used.

Figure 2A:
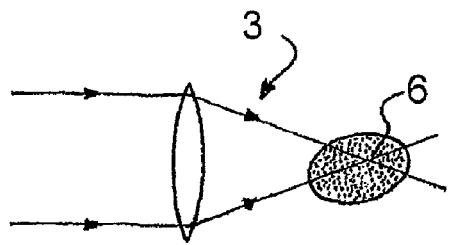
FIGS. 2a and 2b show how the microscope optics of the apparatus can be arranged to have low numerical aperture or high numerical aperture.
Figure 2B:
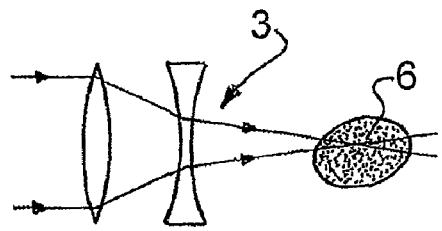

The microscope optics 3 may have a high numerical aperture (FIG. 2a) or may be adapted to have a low numerical aperture (FIG. 2b) which is useful for some specimens to be imaged.

Figure 3:
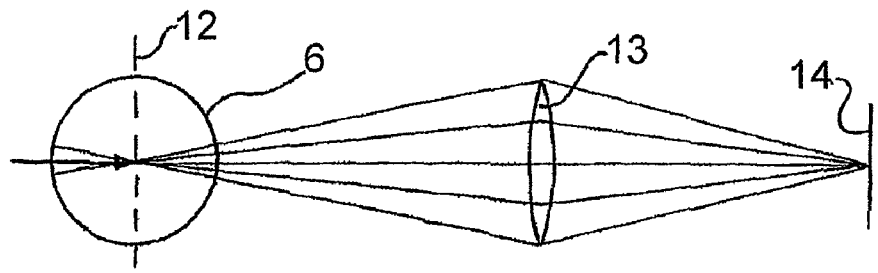
FIG. 3 shows known image-forming optics.

FIG. 3 illustrates a known image-forming system. The light from any point on the focal plane 12 (within the specimen) is collected and refracted by a lens 13 towards a single point in the image plane 14. There exists a symmetry such that any point on the image plane 14 maps to a point in the focal plane 12 and vice versa.

Figure 4:
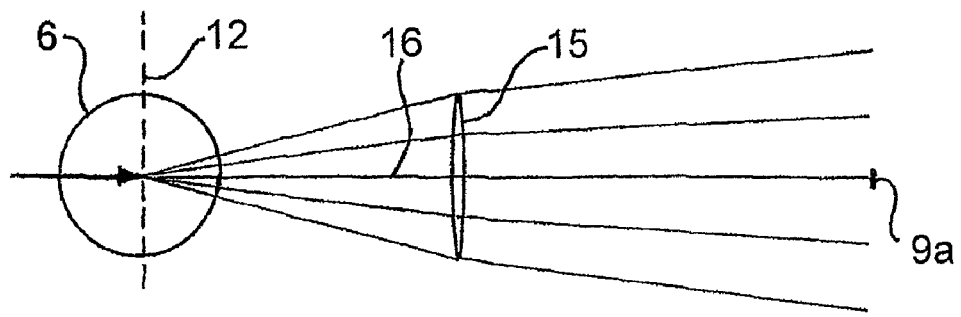
FIGS. 4 and 5 show the image-forming optics of an optical system of the inventive apparatus.
Figure 5:
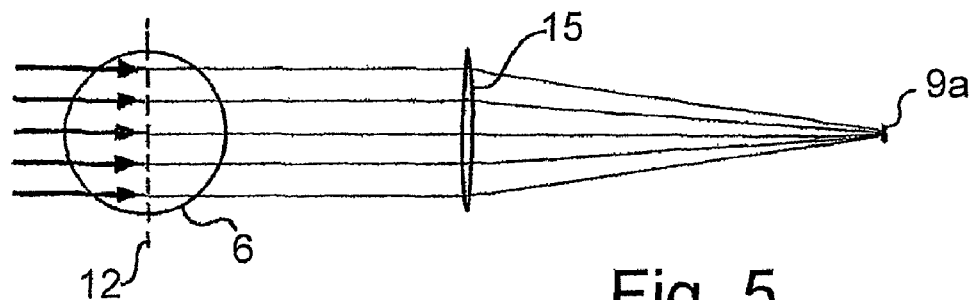

By contrast, the need for an image forming optical arrangement is removed in the inventive "non-focal" optics of FIGS. 4 and 5 which displays no such symmetry. The non-focal optical system 8 is represented by a convex lens 15. The light from a single point on the focal plane 12 is not focussed onto a single light detector. It is diverged such that only the light which exits or by-passes the specimen 6 parallel to the incident beam reaches the single light detector 9a positioned on the optical axis. The purpose of the lens 15 in FIGS. 4 and 5 is different from FIG. 3. It functions in a light-scanning situation. The light beam is scanned (e.g. in a raster pattern) across the specimen through a multitude of different positions (five of which are illustrated as the black arrows in FIG. 5). The purpose of the non-focal optical system 8 (i.e. the lens 15) is to direct onto the single light detector 9a, light which exits or by-passes the specimen parallel to the incident beam, irrespective of the scanning position of the light beam. In specimens which cause significant scattering of light the system allows a higher signal-to-noise ratio to be obtained by limiting detection of scattering light.

FIGS. 6a to 6d, which illustrate scattering as an example to show deviation from the original beam position, illustrate some representative light paths for rays (derived from a laser beam) emitted from the specimen 6 while passing through the non-focal optical system. The beam approaching the specimen from the left is the beam incident on the specimen.

Figure 6A:
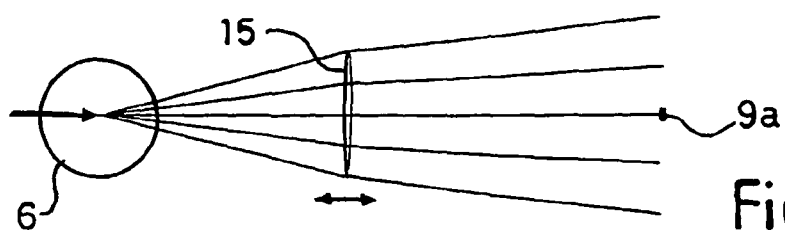
FIGS. 6a, 6b, 6c and 6d show representative light paths for the optical system of the inventive apparatus.

In FIG. 6a rays scattered from a point in the centre of the specimen 6 are diverged away from the light detector 9a. The proportion of scattered rays which are detected can be adjusted by changing the effective size of the detector. An adjustable iris allows this control (which is very similar to the pin-hole in a scanning confocal microscope). Alternatively, the position of the lens can be adjusted to cause more or less divergence of the scattered rays. In optical image-forming systems, an airy disc is the interference pattern produced by the light emitted from a single point within the specimen. Optical systems which produce larger airy discs have lower resolving power, as airy discs from neighbouring points within the specimen will overlap. The concept of the airy disc is not strictly relevant to a projection-measuring system like this, however a similar concept does exist. In the case of the non-focal optics described here, light from each projection creates a very broad distribution of intensities (at the position of the detector) similar to a broad airy disc, which might suggest low resolving power. However, as only a single projection is measured at any one time even very broad distributions cannot interfere with each other.

Figure 6B:
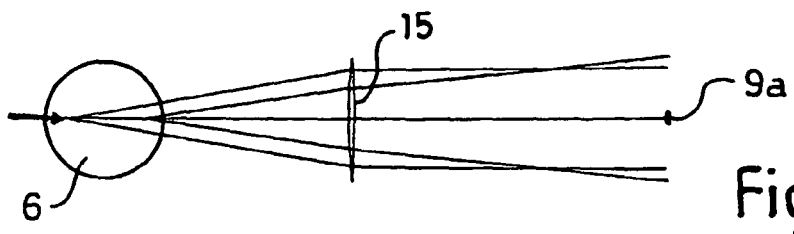

In FIG. 6b rays scattered from other points along the same line sampled in FIG. 6a, are also diverged away from the light detector 9a.

Figure 6C:
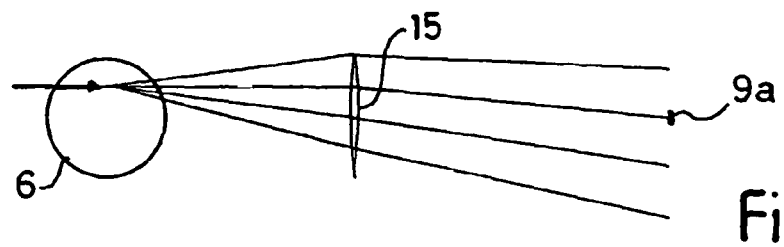

In FIG. 6c unscattered light from a different scanned position (black arrow) is emitted from the specimen 6 substantially parallel to the optical axis, and is therefore refracted towards the light detector 9a. As in FIGS. 6a and 6b, scattered light is directed away from the detector 9a.

Figure 6D:
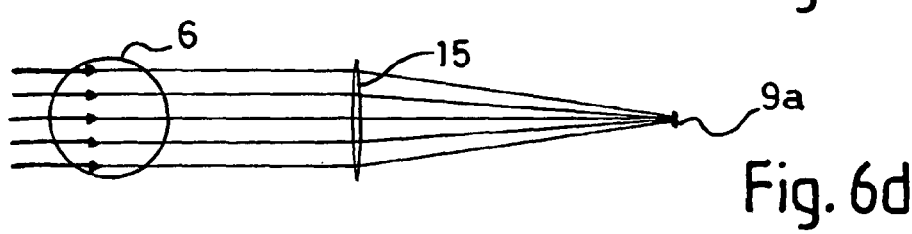

In FIG. 6d unscattered rays from any scanned position are directed onto the light detector 9a. The arrows represent successive positions of the laser beam as it is scanned across the specimen 6 in a direction perpendicular to the optical axis.

All experiments done so far with optical projection tomography have had to assume that although some of the light is scattered, the refractive index of the specimen is uniform. Recent experiments have demonstrated that a number of important specimens (including medical imaging of biopsies) display non-uniform refractive indexes. This means that the current algorithms are not accurately imaging the specimen—distortions and artefacts are introduced. The apparatus described reduces this problem by measuring information not previously available relating to the angle at which a light beam exits from the specimen. In general, in specimens with low scattering but non-uniform distribution of refractive index the system allows this non-uniform distribution to be calculated by measuring the degree of refraction experienced by each projection.

Figure 7A:
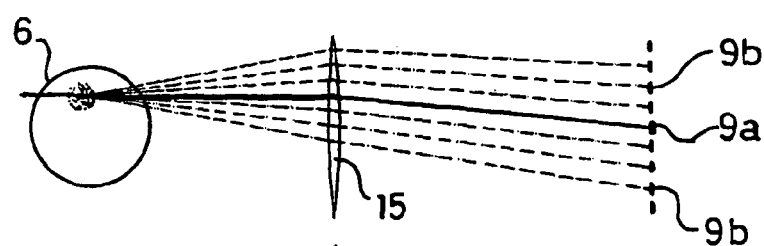
FIGS. 7a, 7b and 7c illustrate how different degrees of refraction affect operation of the optical system.

In the use of the present apparatus a clearing agent (such as BABB) is used such that the majority of the light is not scattered. It is however subject to a different form of disruption-refraction. In FIG. 7, scattered light is indicated by broken lines, while the main path of light is shown as a solid line. In the first example of FIG. 7a this path is not bent as it passes through the specimen 6 (it is only refracted on passing through the lens). The main path does pass through a region of the specimen with a higher refractive index than the rest (grey disc), however both the interfaces it encounters between regions of differing refractive index are perpendicular to the light path, so no refraction occurs.

Figure 7B:
Figure 7C:
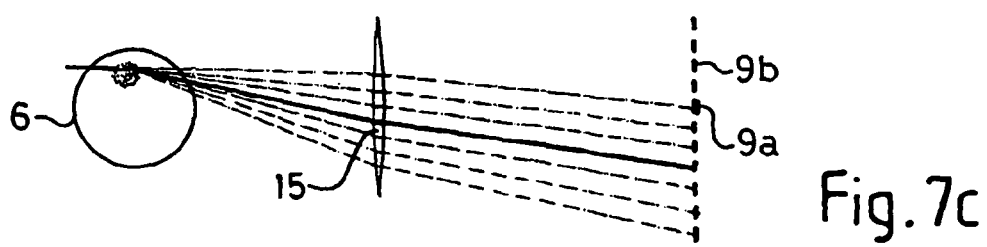

In the second case of FIG. 7b, the illumination beam is slightly higher and therefore the interfaces it encounters between the grey region and the white region of the specimen (different refractive indexes) are slightly displaced from perpendicular. This causes two slight refractions of the main path such that when the light emerges from the specimen it is no longer parallel to the incident beam and is directed slightly to the side of the original central light detector 9a. If auxiliary light detectors 9b are positioned on either side of the central detector 9a, these can measure the degree of refraction. Any projection will give a certain distribution of intensities along the array of light detectors. The distribution of intensities can be used to determine the angle at which the main light path emerged from the specimen. In the last case of FIG. 7c, a different scanned position has caused greater refraction of the beam, which is reflected in a further shift along the array of detectors.

Figure 8:
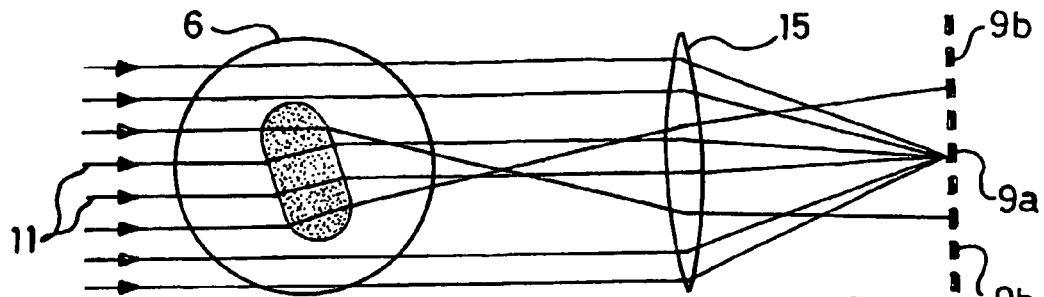
FIG. 8 illustrates how refraction is measured using a one-dimensional array of detectors.

In FIG. 8, an oblong region of the specimen 6 has a higher refractive index (grey shape) than the rest. Rays passing around the specimen are not refracted and so are directed to the central light detector 9a. Rays passing through the middle of the specimen (middle two rays 11 in FIG. 8) are refracted twice. The two interfaces which the light passes through (white-to-grey and then grey-to-white) are parallel with each other, and the light rays therefore exit the specimen at the same angle that they entered it. These rays are also directed onto the central detector 9a. Rays passing through other parts of the grey region are also refracted twice but do not pass through parallel interfaces, so these rays are detected by the adjacent light detectors 9b.

The fact that some rays will be refracted and still exit the specimen 6 parallel to the incident beam is not a problem. The example of FIG. 8 shows only one of the many sets of projections taken through this section. Full imaging involves capturing such a data set for many orientations through the section, and the combination of all this data allows a full reconstruction of the distribution.

Figure 9:
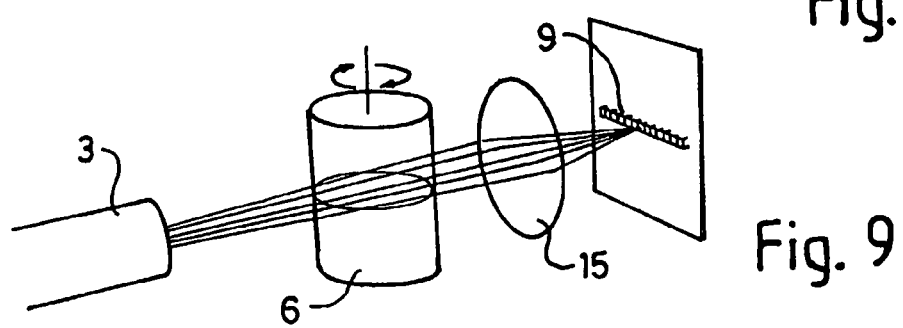
FIGS. 9 to 12 illustrate, in three dimensions, the operation of the optical system.

FIGS. 9 to 12 show three-dimensional views of the apparatus. In FIG. 9, all unrefracted (and unscattered) rays through a two-dimensional section of the specimen are focussed onto the central light detector of the array. The specimen 6 is rotated about a vertical axis between indexed positions in each of which a complete scan is undertaken.

Figure 10:
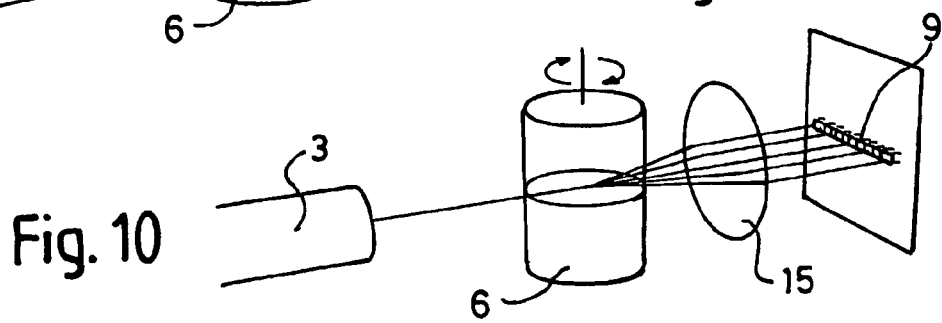

FIG. 10 shows the path of scattered or refracted light onto auxiliary light detectors.

Figure 11:
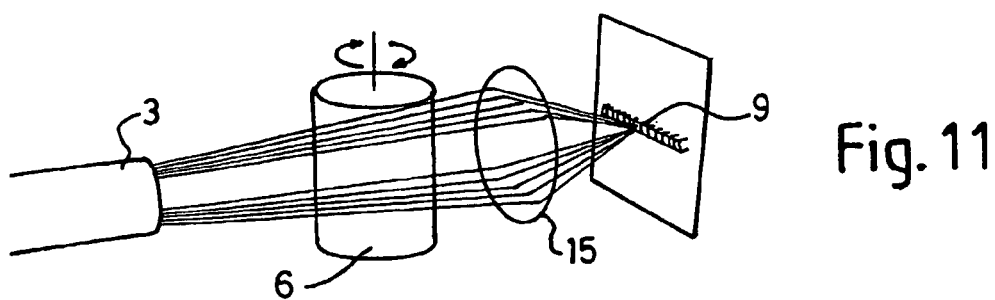

FIG. 11 illustrates that the lens (or optical system) allows the one-dimensional array of detectors 9 to capture data from a full two-dimensional raster-scan of the specimen. A row of scanned positions is always directed down or up to the row of detectors, irrespective of the vertical height of the scan.

Figure 12:
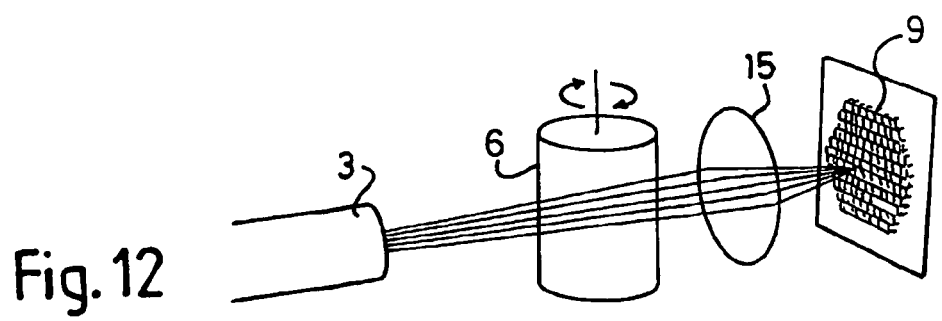

A two-dimensional array of light detectors 9 may be used instead of a one-dimensional array, as shown in FIG. 12. This would be able to measure light which is scattered or refracted above or below the plane occupied by the light rays shown in FIG. 12.

The data derived from the detector array 9 optics is interpreted by an algorithm.

Many different algorithmic approaches already exist for performing back-projection calculations. One approach is to use a standard linear filtered back-projection algorithm (as in U.S. Pat. No. 5,680,484). Other approaches include iterative, maximum entropy and algebraic reconstruction technique. (R. Gordon et al., "Three-Dimensional Reconstruction form Projections: A Review of Algorithms".

The algorithm works as follows:

1. The data is used as if it were parallel (or fan-beam) data to perform back-projection. This produces a "fuzzy" estimation of the distribution of absorption characteristics of the specimen, or alternatively a fuzzy distribution of the fluorescence of the specimen.
2. A first approximation of the distribution of refractive index is estimated. This can be done in a number of ways. One useful method is to assume that the absorption or fluorescent distribution will reflect the distribution of refractive index. Within each section a 2-D gradient vector is calculated for each voxel. An alternative is to start with a uniform or a random distribution.
3. The estimated refraction distribution is used to perform a forward-projection, i.e. a prediction of what the projection data should look like if the initial estimate of the refraction distribution was correct.
4. The predicted projections and the actual projections are compared.
5. The estimated refraction distribution is modified. The projections with a greater difference between predicted and actual, pin-point which regions of the distribution need more modification. For example, in the case of the grey shape shown in FIG. 8, projections from the curved ends of the oblong will differ greatly from the predictions due to the large amount of refraction. Voxels in the regions therefore have their predicted refraction indexes changed more than other regions.
6. The loop from 3 to 6 is repeated until no further improvements to the predicted projections can be made.

The algorithm approach above can also be used to interpret other optical signals, for example fluorescence or scattering.

Samples for use in the present invention may be prepared employing conventional pathological and histological techniques and procedures well known to persons skilled in the art.

For example, in-situ hybridisation (particularly useful for detecting RNAs): Hammond K L, Hanson I M, Brown A G, Lettice L A, Hill R E "Mammalian and *Drosophila* dachsund genes are related to the Ski proto-oncongene and are expressed in eye and limb". Mech Dev. 1998 June; 74(1-2): 121-31.

Immunohistochemistry (particularly useful for detecting proteins and other molecules): Sharpe J, Ahlgren U, Perry P, Hill B, Ross A, Hecksher-Sorensen J, Baldock R, Davidson D. "Optical projection tomography as a tool for 3D microscopy and gene expression studies" Science. 2002 Apr. 19; 296(5567):541-5.

It will be appreciated that modification may be made to the invention without departing from the scope of the invention.

The invention claimed is:

1. Apparatus for obtaining an image of a specimen by optical projection tomography, the apparatus comprising light scanning means, a rotary stage for rotating the specimen to be imaged, an optical system and a localized light detector, wherein light from the scanning means scans the specimen and the optical system is constituted by a convex lens which causes convergence of light incident thereon and is operative to direct onto only the localized light detector throughout the scanning movement of the light that light which exists or by-passes the specimen parallel to a beam incident on the specimen, thereby to allow a higher signal-to-noise ratio by limiting detection of scattered light at the localized light detector.

2. Apparatus according to claim 1, wherein the localized light detector is one detector of a linear array of detectors, the other detectors of the array constituting auxiliary detectors which detect scattered and/or refracted light.

3. Apparatus according to claim 1, wherein the localized light detector is one detector of a two-dimensional array of detectors, the other detectors of the array constituting auxiliary detectors which detect scattered and/or refracted light.

4. Apparatus according to claim 1, wherein the rotary stage rotates the specimen to indexed positions in each of which the specimen is in use subjected to a scanning movement of incident light by the scanning means.

5. Apparatus according to claim 4, wherein the scanning means is operative to scan the light in a raster pattern, one complete raster scan being undertaken at each indexed position of the specimen.

6. Apparatus according to claim 1, wherein the light scanning means is part of a confocal scanning microscope.

* * * * *